United States Patent
Soukup et al.

[11] Patent Number: 5,466,252
[45] Date of Patent: Nov. 14, 1995

[54] IMPLANTABLE LEAD

[75] Inventors: Thomas M. Soukup; Richard A. Staley, both of Flagstaff, Ariz.

[73] Assignee: W. L. Gore & Associates, Inc., Newark, Del.

[21] Appl. No.: 955,611

[22] Filed: Oct. 2, 1992

[51] Int. Cl.⁶ ............................. A61N 1/04; H01B 7/08
[52] U.S. Cl. ................... 607/116; 128/642; 174/120 AR
[58] Field of Search ........................... 128/419 C, 419 P, 128/420.6, 642, 673, 692, 784–786, 803, 899, D14; 607/96, 98–102, 115–119, 122–126, 129; 174/120 R, 120 AR, 120 SR

[56] References Cited

U.S. PATENT DOCUMENTS

| | | |
|---|---|---|
| 4,033,355 | 7/1977 | Amundson . |
| 4,304,010 | 12/1981 | Mano . |
| 4,573,480 | 3/1986 | Hirschberg . |
| 4,816,339 | 3/1989 | Tu et al. . |
| 4,840,186 | 6/1989 | Lekholm et al. . |
| 4,877,661 | 10/1989 | House et al. ............... 428/34.9 |
| 4,947,866 | 8/1990 | Lessar et al. ............... 128/784 |
| 4,955,899 | 9/1990 | Della Corna et al. . |
| 4,964,414 | 10/1990 | Handa et al. ............... 128/784 |
| 4,972,846 | 11/1990 | Owens et al. . |
| 5,007,435 | 4/1991 | Doan et al. ............... 128/784 |
| 5,016,646 | 5/1991 | Gotthardt et al. ............... 128/784 |
| 5,115,818 | 5/1992 | Holleman et al. ............... 128/784 |

FOREIGN PATENT DOCUMENTS

| | | |
|---|---|---|
| 0388480 | 9/1990 | European Pat. Off. . |
| 9211061 | 7/1992 | WIPO . |

*Primary Examiner*—William E. Kamm
*Assistant Examiner*—Marianne Parker
*Attorney, Agent, or Firm*—Wayne D. House

[57] ABSTRACT

An implantable lead for use with cardiac pacemakers, defibrillators and other long term implantable electrical devices intended for sensing or tissue stimulation, having a helically wound conductor with a surrounding tubular insulating layer of elastomeric material such as silicone or polyurethane and an additional coaxial tubular exterior biocompatible layer of porous PTFE having a microstructure of nodes interconnected by fibrils. The exterior tubular layer of porous PTFE may be fitted coaxially over the elastomeric tubular layer whereby the porous PTFE tubular layer is in longitudinal compression and the fibrils within the microstructure have a bent and wavy appearance. Any portion of the length of the porous PTFE tubing in longitudinal compression allows that portion of the length of the lead wire to be extensible to a controlled extent limited by the straightening of the bent fibrils within the porous PTFE microstructure.

24 Claims, 3 Drawing Sheets

IMPLANTABLE LEAD

FIELD OF THE INVENTION

This invention relates to the field of implantable electrical leads for use with various implantable electrical devices such as cardiac pacers and defibrillators.

BACKGROUND OF THE INVENTION

Conventional implantable leads for use with implantable electrical devices such as cardiac pacemakers and defibrillators are typically constructed of a helically wound conductor having an outer insulation layer of tubular form surrounding the wire helix. The tubular insulation is most commonly of an elastomeric material such as silicone or polyurethane. The combination of a helically wound conductor with elastomeric outer insulation provides these conventional constructions with a substantial amount of potential elastic deformation in the direction of the length of the lead.

The fundamental requirements of implantable leads are that they must have excellent mechanical integrity, electrical insulating properties and biocompatibility, and must be flexible with a long flex life to accommodate attachment to a beating heart.

Conventional implantable leads have several disadvantages. The silicone or polyurethane outer coverings are not ideally biocompatible and are frequently known to provoke adverse tissue reactions over time. Polyurethane outer coverings are known to crack under stress. Silicone outer coverings are vulnerable to abrasion over time. Additionally, these conventional leads are known to break during attempts to remove them from implanted patients by the application of a tensile force. In these cases the remaining portion must be abandoned within the patient's body or must be surgically removed.

Implantable lead wires using insulation materials other than the conventional silicones or polyurethanes have been described previously. U.S. Pat. No. 4,573,480 describes an implantable electrode lead in the form of a helically wound conductor having a tubular insulating layer surrounding the helically wound wire wherein the tubular insulating layer is porous polytetrafluoroethylene (hereinafter PTFE) having a pore size limited to a maximum size described as "being essentially impervious to body fluids to prevent tissue growth thereon." This pore size is described as being not larger than 4 microns. While pore sizes of this range and smaller are known to preclude cellular ingrowth, the material remains pervious to body fluids which will wet out such an insulating layer shortly after implantation. The result is that the effectiveness of the electrical insulation is destroyed. Alternatively, this patent teaches that the tubular porous PTFE insulating layer may be provided with an outer covering of smooth and impervious material. While this alternative construction prevents the wetting out of the porous PTFE layer by body fluids, it loses the biocompatible advantage provided by the tissue contacting outer surface of porous expanded PTFE.

SUMMARY OF THE INVENTION

The present invention is an implantable lead having improved tensile strength, excellent flexibility, excellent insulating characteristics, improved biocompatibility and controlled amounts of elongation during the application of tension to the lead. The amount of elongation may be varied over different portions of the length of the lead.

The implantable lead comprises a helically wound electrical conductor having a layer of elastomeric insulating tubing coaxially surrounding the helix formed by the helically wound conductor. The layer of elastomeric insulating tubing is in turn coaxially surrounded by a layer of porous PTFE tubing having a microstructure of nodes interconnected by fibrils. At least a portion of the length of the porous PTFE may be under longitudinal compression whereby the fibrils of the microstructure within that portion of the length have a substantially bent and wavy appearance. Consequently this portion of the length may be stretched or extended until the fibrils of the microstructure are straightened as a result of tension applied to that portion of the lead. The entire length of a lead may be provided with an exterior covering of longitudinally compressed porous PTFE tubing if desired.

The term coaxial is herein used in relationship to the longitudinal axis of the helix formed by the at least one helically wound conductor.

The porous PTFE outer covering provides the lead wire with excellent flexibility, biocompatibility and tensile strength while simultaneously providing the lead with a controlled amount of extensibility.

The fibril length of the porous PTFE must be adequate to provide the necessary amount of flexibility and extensibility for the intended application and preferably should be of adequate size to present an acceptable biocompatible surface to the blood chemistry to which the outer surface of the lead will be exposed. The preferred fibril lengths are greater than about 4 microns and most preferably greater than about 10 microns. Fibril length is measured as taught by U.S. Pat. No. 4,972,846.

The layer of tubular elastomeric insulation surrounding the helically wound conductor provides excellent insulation because these materials are substantially impervious to body fluids. They are disadvantageous as the exterior surface of a lead because they are not ideally biocompatible and are known in some patients to provoke adverse tissue reactions. The additional exterior covering of porous PTFE tubing of the lead of the present invention provides a superior biocompatible surface. While this porous exterior covering is likely to be wet out by body fluids and is consequently inadequate by itself as an effective electrical insulation material for purposes of implantation in living bodies, the combination of a porous PTFE exterior covering surrounding a layer of impervious elastomeric insulating tubing offers a superior biocompatible lead insulation.

The at least one helically wound conductor wire used with the present invention may be a single conductor or alternatively may be multiple-filar if more than one conductor is required for a desired application.

The porous PTFE having a microstructure of nodes interconnected by fibrils used for the exterior tubular covering of the inventive lead is made according to the teachings of U.S. Pat. No. 4,187,390 and 3,953,566. The tubular covering of porous PTFE may be provided with bent or wavy fibrils resulting in stretch characteristics in a similar manner to that taught by U.S. Pat. Nos. 4,877,661 and 5,026,513.

DETAILED DESCRIPTION OF THE INVENTION

Figure 1:
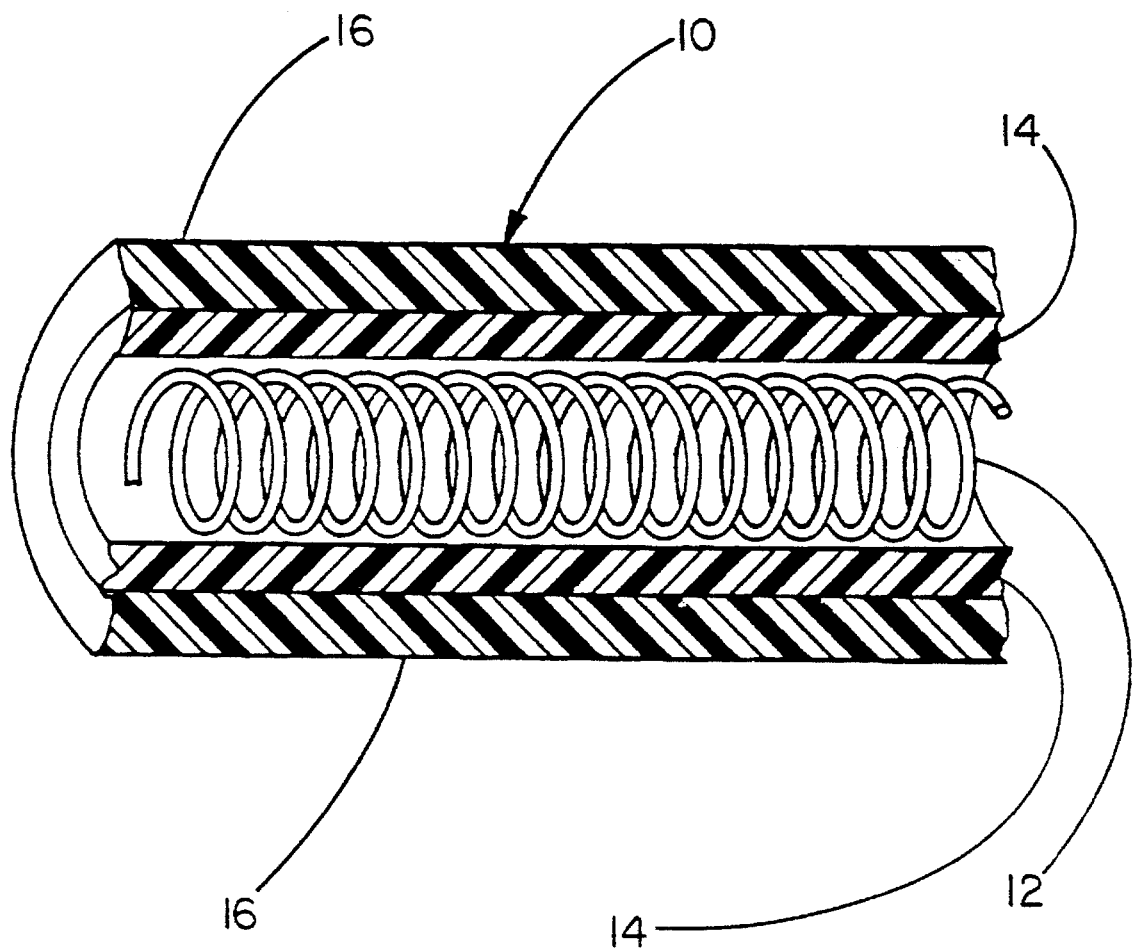
FIG. 1 describes a cross section of the implantable lead of the present invention wherein a helically wound electrical conductor is coaxially covered by a layer of tubular elastomeric insulation which is in turn coaxially covered by an exterior tubular layer of porous PTFE having a microstructure of nodes interconnected by fibrils.

FIG. 1 describes a cross section of the implantable lead 10 of the present invention wherein a helically wound electrical conductor 12 is coaxially covered by a tubular layer of an elastomeric electrically insulating material 14 such as silicone or polyurethane. The lead is further provided with an exterior coaxial tubular covering of porous PTFE 16 having a microstructure of nodes interconnected by fibrils.

Elastomeric materials are herein defined as polymeric materials which at room temperature can be stretched under low stress to at least twice their original length and, immediately upon release of the stress, will recover with force to their approximate original length.

Figure 2:
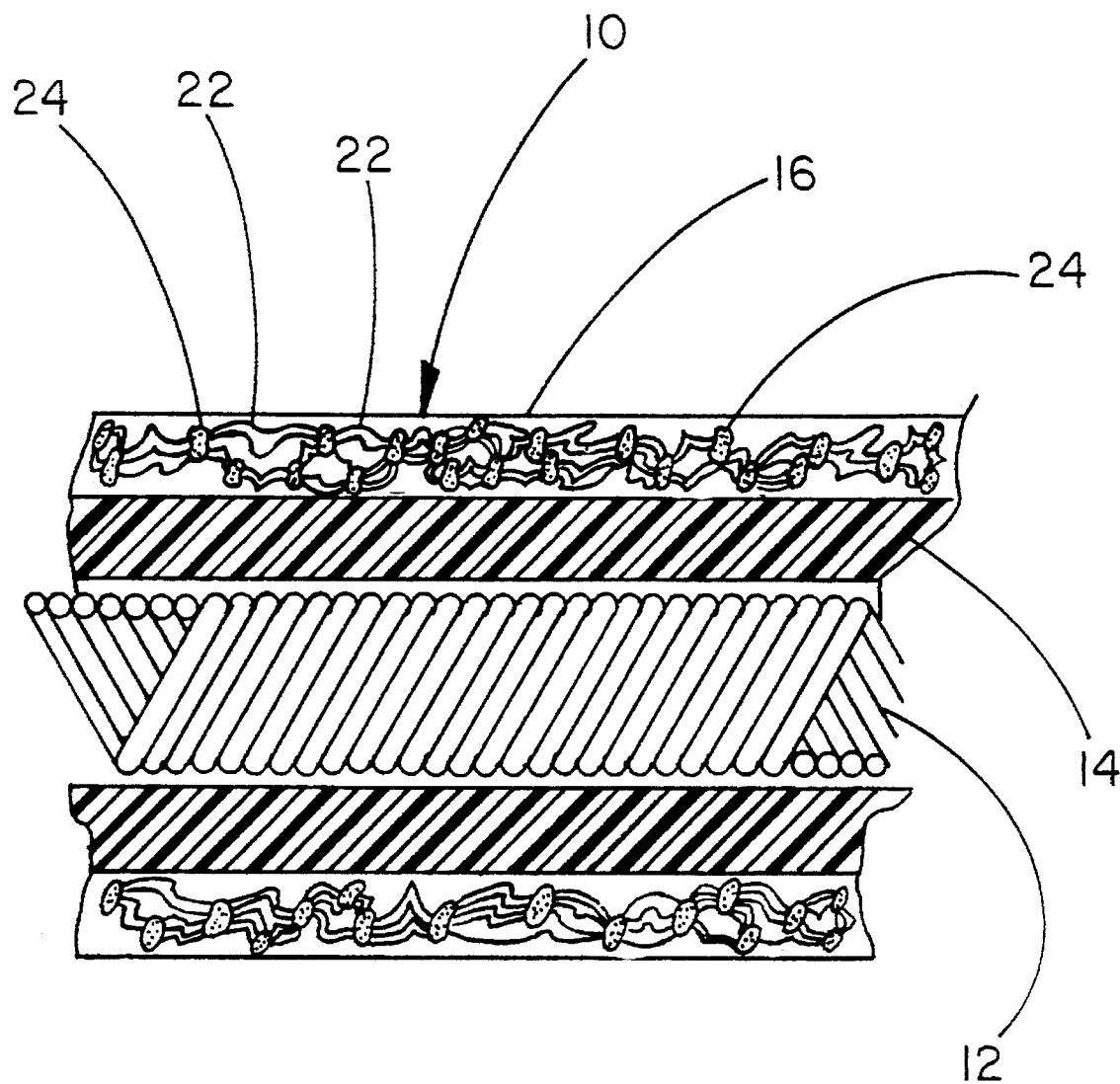
FIG. 2 describes a cross section of the implantable lead of one embodiment of the present invention wherein the exterior tubular layer of porous PTFE is shown under longitudinal compression wherein the fibrils of the microstructure have a bent and wavy appearance.
Figure 3:
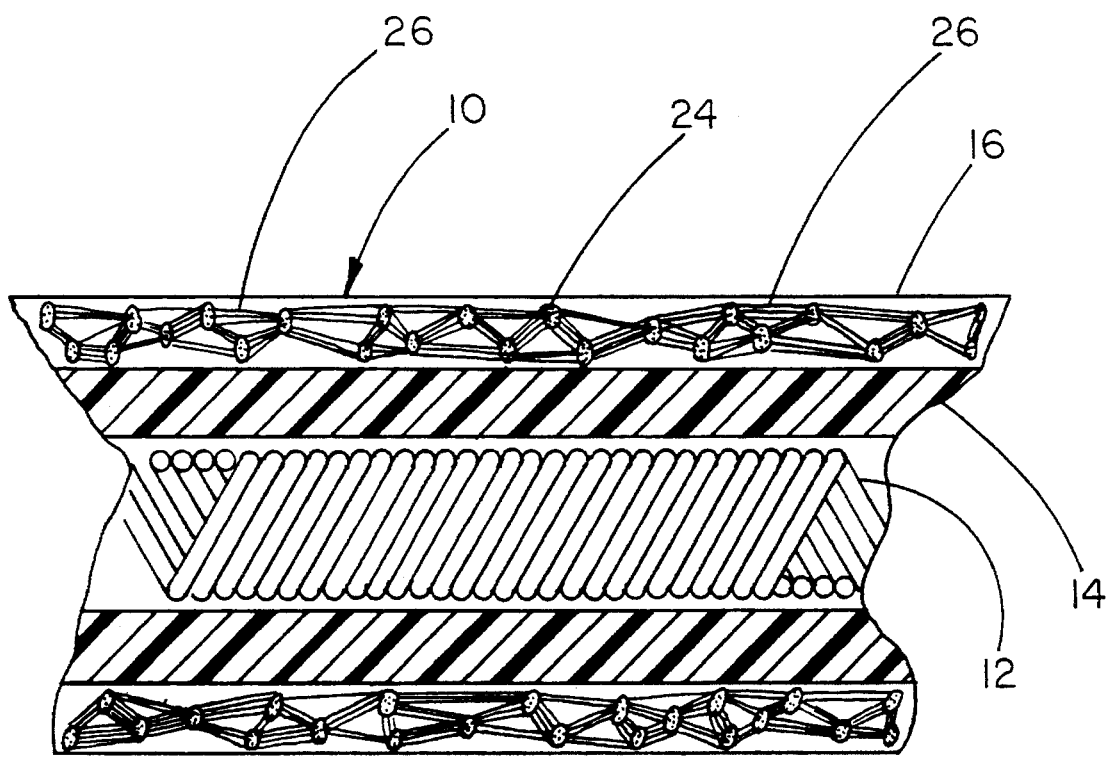
FIG. 3 describes a cross section of the implantable lead of one embodiment of the present invention wherein the exterior tubular layer of porous PTFE is shown under tension wherein the fibrils of the microstructure are substantially straight.

FIGS. 2 and 3 describe cross sections of a preferred embodiment wherein FIG. 2 shows the lead in a relaxed state and FIG. 3 shows the lead under longitudinal tension. As shown by FIG. 2, if the exterior covering of porous PTFE tubing is fitted around the tubular elastomeric insulating layer so that the porous PTFE tubing is under some degree of longitudinal compression, the fibrils 22 that interconnect the nodes 24 within the microstructure of the porous PTFE 10 tubing 16 will assume a bent and wavy appearance due to the longitudinal compression applied to the porous PTFE tubing 16 when it is fitted over the elastomeric tubing 14 during construction of the lead.

When longitudinal tension is applied to the lead as shown by FIG. 3, the spring characteristic of the helically wound conductor 12 and the elastic characteristic of the elastomeric tubing 14 allow those components of the lead construction to extend longitudinally. Additionally, the bent fibrils 22 of the porous PTFE tubing 16 as shown previously in FIG. 2, are able to extend until they become straight and taut fibrils 26 as a result of the applied tension, as shown by FIG. 3. It is apparent that the amount of extension of the porous PTFE tubing is a function of the amount of longitudinal compression applied to the porous PTFE tubing during construction of the lead and the resulting amount of bending that is applied to the fibrils.

The exterior tubular covering of porous PTFE 16 is fitted over the exterior surface of the elastomeric tubing 14. The relationship between the inside diameter of the porous PTFE tubing and the outside diameter of the elastomeric tubing should be such that there is at most only a small amount of interference when these respective diameters are measured with the tubes in relaxed states with no tension applied. Preferably there is no interference between these respective diameters.

The porous PTFE tubing 16 is most easily fitted over the elastomeric tubing 14 prior to inserting the helically wound conductor into the bore of the elastomeric tubing. This avoids any risk to the conductor. For constructions involving a slight interference fit between the respective diameters of the two tubes, the elastomeric tubing 14 may be placed under tension adequate to cause a significant reduction in its outside diameter before fitting it into the exterior porous PTFE tubing. This tension is preferably applied with a pull-wire attached to the ends of the bore of the elastomeric tubing, thereby not interfering with access to the exterior surface of the elastomeric tubing. The exterior tubular covering of porous PTFE is then fitted over the reduced diameter of the tensioned elastomeric tube.

After the exterior tubular covering of porous PTFE has been fitted over the tensioned elastomeric tubing, the tension on the elastomeric tubing is released. The diametrical interference between the porous PTFE tubing and the elastomeric tubing results in the securing of the two tubes together. Alternatively, a biocompatible adhesive such as a silicone adhesive may be used during the construction process.

The porous PTFE tube is longitudinally compressed according to the amount of extensibility, if any, that is desired of the completed implantable lead. The longitudinal compression can be uniformly applied over the chosen length of porous PTFE tubing or alternatively the compression can be applied non-uniformly if it is desired to have different extensibility characteristics over different parts of the lead.

The helically wound conductor is preferably fitted into the bore of the elastomeric tubing after completion of the insulation construction. The at least one helically wound conductor wire used with the present invention may be a single conductor or alternatively may be multiple-filar if more than one conductor is required for a desired application. Multiple conductors will require that the individual conductors be separately insulated from each other, preferably by a layer of insulation covering the surface of each individual conductor. In the case of a single helically wound conductor, the conductor may optionally be separately insulated within the two-layer coaxially oriented insulation of the present invention. Insulation covering the surface of helically wound conductors is preferably applied to each conductor surface prior to helical winding of the conductors.

For cardiac pacemaker and defibrillator lead applications, the conductor is preferably a MP35N nickel alloy stainless steel material.

We claim:

1. An implantable lead comprising:

a) at least one helically wound electrical conductor;

b) a tubular covering of an elastomeric polymer having a length, said tubular covering of an elastomeric polymer coaxially surrounding the at least one helically wound electrical conductor, wherein said tubular covering of an elastomeric polymer is substantially impervious to body fluids; and c) an exterior tubular covering of porous polytetrafluoroethylene having a length and having a microstructure of nodes interconnected by fibrils wherein the exterior tubular covering of porous polytetrafluoroethylene coaxially surrounds the tubular covering of an elastomeric polymer, and wherein the exterior tubular covering of porous polytetrafluoroethylene is pervious to body fluids.

2. An implantable lead according to claim 1 wherein the elastomeric polymer is a thermoset elastomeric polymer.

3. An implantable lead according to claim 2 wherein teh thermoset elastomeric polymer is silicone.

4. An implantable lead according to claim 3 wherein at least a portion of the length of the exterior tubular covering of porous polytetrafluoroethylene is adhered to at least a portion of the length of the tubular covering of elastomeric polymer by a silicone adhesive.

5. An implantable lead according to claim 1 wherein the elastomeric polymer is a thermoplastic elastomeric polymer.

6. An implantable lead according to claim 5 wherein the thermoplastic elastomeric polymer is polyurethane.

7. An implantable lead according to claim 1 wherein at least a portion of the length of the exterior covering of porous polytetrafluoroethylene has a microstructure of nodes interconnected by bent fibrils and the portion of the length of exterior covering of porous polytetrafluoroethylene is elastically stretchable and recoverable, and wherein the portion of the length of exterior covering of porous polytetrafluoroethylene is stretchable to a length equal to at least 1.2 times the length of the porous polytetrafluoroethylene covered portion of the implantable lead before stretching.

8. An implantable lead according to claim 7 wherein the portion of the length of the exterior covering of porous polytetrafluoroethylene is elastically stretchable and recoverable wherein the portion of the length of exterior covering of porous polytetrafluoroethylene is stretchable to a length equal to at least 1.5 times the length of the porous polytetrafluoroethylene covered portion of the implantable leads before stretching.

9. An implantable lead comprising:

a. at least one helically wound electrical conductor;

b. a tubular covering of an elastomeric polymer having a length, said tubular covering of an elastomeric polymer coaxially surrounding the at least one helically wound electrical conductor; and c. an exterior tubular covering of porous polytetrafluoroethylene having a length and having a microstructure of nodes interconnected by fibrils wherein the exterior tubular covering of porous polytetrafluoroethylene coaxially surrounds the tubular covering of an elastomeric polymer, wherein the fibrils have an average length greater than about 4 microns.

10. An implantable lead according to claim 9 wherein the fibrils have an average length greater than about 10 microns.

11. An implantable lead according to claim 10 wherein the elastomeric polymer is a thermoset elastomeric polymer.

12. An implantable lead according to claim 11 wherein the thermoset elastomeric polymer is silicone.

13. An implantable lead according to claim 12 wherein at least a portion of the length of the exterior tubular covering of porous polytetrafluoroethylene is adhered to at least a portion of the length of the tubular covering of elastomeric polymer by a silicone adhesive.

14. An implantable lead according to claim 10 wherein the elastomeric polymer is a thermoplastic elastomeric polymer.

15. An implantable lead according to claim 14 wherein the thermoplastic elastomeric polymer is polyurethane.

16. An implantable lead according to claim 10 wherein at least a portion of the length of the exterior covering of porous polytetrafluoroethylene has a microstructure of nodes interconnected by bent fibrils and the portion of the length of exterior covering of porous polytetrafluoroethylene is elastically stretchable and recoverable, and wherein the portion of the length of exterior covering of porous polytetrafluoroethylene is stretchable to a length equal to at least 1.2 times the length of the porous polytetrafluoroethylene covered portion of the implantable lead before stretching.

17. An implantable lead according to claim 10 wherein at least a portion of the length of the exterior covering of porous polytetrafluoroethylene has a microstructure of nodes interconnected by bent fibrils and the portion of the length of exterior covering of porous polytetrafluoroethylene is elastically stretchable and recoverable, and wherein the portion of the length of exterior covering of porous polytetrafluoroethylene is stretchable to a length equal to at least 1.5 times the length of the porous polytetrafluoroethylene covered portion of the implantable lead before stretching.

18. An implantable lead according to claim 9 wherein the elastomeric polymer is a thermoset elastomeric polymer.

19. An implantable lead according to claim 18 wherein the thermoset elastomeric polymer is silicone.

20. An implantable lead according to claim 19 wherein at least a portion of the length of the exterior tubular covering of porous polytetrafluoroethylene is adhered to at least a portion of the length of the tubular covering of elastomeric polymer by a silicone adhesive.

21. An implantable lead according to claim 9 wherein the elastomeric polymer is a thermoplastic elastomeric polymer.

22. An implantable lead according to claim 21 wherein the thermoplastic elastomeric polymer is polyurethane.

23. An implantable lead according to claim 9 wherein at least a portion of the length of the exterior covering of porous polytetrafluoroethylene has a microstructure of nodes interconnected by bent fibrils and the portion of the length of exterior covering of porous polytetrafluoroethylene is elastically stretchable and recoverable, and wherein the portion of the length of exterior covering of porous polytetrafluoroethylene is stretchable to a length equal to at least 1.2 times the length of the porous polytetrafluoroethylene covered portion of the implantable lead before stretching.

24. An implantable lead according to claim 9 wherein at least a portion of the length of the exterior covering of porous polytetrafluoroethylene has a microstructure of nodes interconnected by bent fibrils and the portion of the length of exterior covering of porous polytetrafluoroethylene is elastically stretchable and recoverable, and wherein the portion of the length of exterior covering of porous polytetrafluoroethylene is stretchable to a length equal to at least 1.5 times the length of the porous polytetrafluoroethylene covered portion of the implantable lead before stretching.

* * * * *